(12) United States Patent
Manneschi (10) Patent No.: US 9,335,260 B2
(45) Date of Patent: May 10, 2016

(54) DEVICE FOR ANALYSING COMPOSITION OF CONTENTS OF A CONTAINER

(76) Inventor: Alessandro Manneschi, Arezzo (IT)

( * ) Notice: Subject to any disclaimer, the term of this patent is extended or adjusted under 35 U.S.C. 154(b) by 570 days.

(21) Appl. No.: 12/328,699

(22) Filed: Dec. 4, 2008

(65) Prior Publication Data

US 2009/0146061 A1 Jun. 11, 2009

(30) Foreign Application Priority Data

Dec. 5, 2007 (FR) ...................................... 07 59595

(51) Int. Cl.
| | |
|---|---|
| *G01J 5/02* | (2006.01) |
| *G01N 21/3577* | (2014.01) |
| *G01N 21/90* | (2006.01) |
| *G01N 27/02* | (2006.01) |

(52) U.S. Cl.
CPC ........ *G01N 21/3577* (2013.01); *G01N 21/9027* (2013.01); *G01N 27/023* (2013.01)

(58) Field of Classification Search
CPC ............ G01N 21/9027; G01N 27/023; G01N 21/3577
USPC .................................................... 324/339.12
See application file for complete search history.

(56) References Cited

U.S. PATENT DOCUMENTS

| | | | | |
|---|---|---|---|---|
| 4,485,284 | A * | 11/1984 | Pakulis | ......................... 219/705 |
| 7,442,935 | B2 * | 10/2008 | Manneschi | .............. 250/339.12 |
| 8,030,948 | B2 * | 10/2011 | Manneschi | .......... G01N 27/025 324/637 |
| 2004/0000653 | A1 | 1/2004 | Nordlund | |
| 2007/0228280 | A1 | 10/2007 | Mueller | |
| 2008/0236275 | A1 * | 10/2008 | Breed et al. | .................. 73/290 V |
| 2008/0252305 | A1 * | 10/2008 | Manneschi | .................... 324/693 |
| 2009/0206285 | A1 * | 8/2009 | Manneschi | .................... 250/573 |
| 2015/0185143 | A1 * | 7/2015 | Manneschi | ........ G01N 21/3577 250/339.12 |

FOREIGN PATENT DOCUMENTS

| | | |
|---|---|---|
| DE | 10318893 | 11/2001 |
| EP | 11712900 | 10/2006 |
| GB | 2297377 | 7/1996 |
| JP | 20000193599 | 7/2000 |
| JP | 2006266948 | 10/2006 |

OTHER PUBLICATIONS

Peter Debye; Methods to determine the electrical and geometrical structure of molecules; ; Nobel Lecture; Dec. 12, 1936; pp. 382-401.

* cited by examiner

*Primary Examiner* — Thomas F Valone
(74) *Attorney, Agent, or Firm* — Blakely Sokoloff Taylor & Zafman LLP (57) ABSTRACT

A device for analyzing the composition of the contents of a container. The device includes a transmitter/receiver with an electromagnetic field having at least several frequencies in a determined frequency range, a container support for a container (R) whose contents are to be analyzed. The support is adapted to ensure precise relative positioning between the transmitter/receiver and the container (R). A measuring unit measures the complex impedance of the transmitter/receiver influenced by the load constituted by the container (R) and its contents. A spectral analyzer analyzes the contents of the container for measuring the absorption of waves by the container and its contents. An information providing unit provides information relative to the nature of the contents of the container (R) as a function of the complex measured impedance and of the absorption measuring.

8 Claims, 6 Drawing Sheets

DEVICE FOR ANALYSING COMPOSITION OF CONTENTS OF A CONTAINER

The present invention relates to the field of analysis of the composition of the contents of containers such as bottles.

The present invention can have numerous applications. It can apply especially to production control in bottling plants to avoid any malversation on the contents of containers ultimately supplied to the public. The invention can also apply to checking baggage transported by passengers, in particular hand luggage carried by passengers in airports.

PRIOR ART

Well-known X-ray examination means do not determine the equivalent contents of bottles or containers. Such examination means in fact allow classification into two categories only, organic and non-organic materials. They cannot distinguish between two organic materials.

To eliminate this drawback, a device for analysing the composition of the contents of a container has been developed.

This device comprises transmitter/receiver means of an electromagnetic field with at least several frequencies in a determined frequency range, support means of a container whereof the contents have to be analysed, suitable for ensuring accurate relative positioning between the transmitter/receiver means and the container, means for measuring the complex impedance of the transmitter/receiver means influenced by the load constituted by the container and its contents, representative of the complex dielectric characteristics of the container and its contents, and means for providing information linked to the complex measured impedance and as a consequence to the nature of the contents of said container.

An advantage of this device is that it permits detection of the contents of a container considerably reliably.

To improve reliability of the device described hereinabove, it has already been proposed to introduce thereto means for obtaining at least one additional physical data relative to a characteristic of the container, the information relative to the nature of the contents of the container being a function of the additional physical data, and of the complex measured impedance.

Advantageously, the additional physical data can comprise the mass of the container and its contents.

Recent developments have shown however that certain liquids, available commercially, non-combustible, non-inflammable and non-explosive when intermixed in appropriate proportions, can produce unstable substances apt to explode by means of adequate detonators.

In other cases, mixing two commercially available non-combustible, non-inflammable liquids can engender chemical reactions producing substantial heat and/or emission of toxic fumes.

Some liquids which can be used for producing such dangerous liquid substances (explosive, producing toxic fumes, etc.) have polar behaviour. Their signature is thus identical to water from the electromagnetic point of view.

Currently, there are some differences between the complex dielectric constant of such liquid and water, but this difference can be detected only:

for a container whereof the geometry and the material making it up are known precisely, and
for a quantity of liquid known precisely.

Spectral analysis devices emitting radiation in the infrared spectrum and allowing detection of an inflammable or explosive substance in a container, such as for example a bottle, are also known. The document GB 2 297 377 describes such a spectral analysis device. This device comprises a chamber comprising an opening via which the user vertically places the container to be analysed in the chamber. The device also comprises a cover for capping the opening of the chamber during spectral analysis. This cover limits the effects of ambient light for improving measuring precision.

However, these devices have numerous disadvantages. This type of device especially does not produce reliable analysis results when the container with the liquid to be analysed is for example a bottle made of coloured glass or opaque plastic. Also, this type of device is not adapted to rapid and repeated analysis of different containers, with the user having to make numerous manipulations during each analysis (opening of the cover, withdrawal of the analysed container, introduction of the new container, closing the cover, etc.).

An aim of the invention is to propose a device for improving the reliability and practicability of the above devices, and to facilitate detection of such liquids for production of dangerous substances when intermingled.

BRIEF DESCRIPTION OF THE INVENTION

According to the invention, a device for analysing the composition of the contents of a container is proposed to this end, comprising:

transmitter/receiver means of an electromagnetic field having at least several frequencies in a determined frequency range, support means of a container the contents of which have to be analysed, suitable for ensuring accurate relative positioning between the transmitter/receiver means and the container, means for measuring the complex impedance of the transmitter/receiver means influenced by the load constituted by the container and its contents, representative of the complex dielectric characteristics of the container and its contents, wherein the device further comprises spectral analysis means of the contents of the container for measuring the absorption of waves by the container and its contents, and means for providing information relative to the nature of the contents of said container as a function of the complex measured impedance and of the absorption measuring.

According to another advantageous non limitative aspect of the present invention, the device further comprises:

means for producing at least one additional physical data relative to a characteristic of the container, and means for providing information relative to the nature of the contents of said container as a function of the complex measured impedance and of the additional physical data.

Advantageously, the device according to the invention can comprise the following characteristics:

the spectral analysis means are for sending waves whereof the wavelengths are in the infrared spectrum, and for measuring the absorption of said waves by the container and its contents;

the spectral analysis means are for sending waves whereof the wavelengths are between 0.7 μm and 3 μm;

the spectral analysis means comprise at least one transmitter for sending waves and a receiver placed to receive the waves emitted by the transmitter;

the transmitter and the receiver are placed in the sagittal plane of the support means to the right of one another, such that the waves emitted by the transmitter pass through the container to be analysed prior to being received by the receiver;

the transmitter is placed on the support means and the receiver is placed under the support means;

the transmitter and the receiver are placed in the median plane of the support means opposite one another, such that the waves emitted by the transmitter pass through the container to be analysed prior to being received by the receiver;

the spectral analysis means comprise a plurality of transmitters placed along the support means and a plurality of associated receivers placed to receive the waves emitted by the plurality of transmitters;

the transmitters are placed in the sagittal plane of the support means, said transmitters alternatively being placed on and under the support means, and being associated with receivers placed to the right of said transmitters.

Advantageously, the device according to the invention can further comprise the following characteristics:

means for producing at least one additional physical data relative to a characteristic of the container, the information relative to the nature of the contents of the container being a function of the additional physical data, the additional physical data comprises the mass of the container (R) and its contents.

the means for producing at least one additional physical data comprise a gravimetric sensor for measuring the mass of the container and its contents, the gravimetric sensor is placed under the support means of the container, the tare of the device is measured periodically by the gravimetric sensor when no container is introduced to the support, the presence of a container on the support means is detected by the means for measuring the complex impedance of the transmitter/receiver means, the means for providing information comprise means for correcting the amplitude of the complex measured impedance as a function of the measured mass, comparing the complex corrected impedance with predetermined reference values for the same frequency range, and generating an alarm when the complex measured impedance moves away from the reference values the additional physical data comprises the capacity of the container and/or the material constituting the walls of the container and/or the thickness of the walls of the container, the additional physical data comprises the material constituting the walls of the container, the material being able to be selected from the glass or plastic.

the means for producing at least one additional physical data comprise acquiring means for acquiring the additional physical data, the information relative to the nature of the contents of the container is also a function of the additional physical data acquired by a user on the acquiring means, the means for providing information comprise means for comparing the complex measured impedance with predetermined reference values for the same frequency range, said means commanding the user to acquire the additional physical data on the acquiring means, when the complex measured impedance moves away from the reference values, acquiring the additional physical data due to the acquiring means by selecting characteristics of containers from a predetermined list of container characteristics.

PRESENTATION OF FIGURES

Other characteristics, aims and advantages of the present invention will emerge from the following detailed description, and with reference to the attached drawings, given by way of non-limiting examples and in which.

DESCRIPTION OF THE INVENTION

The present invention is based essentially on the following approach.

Figure 8:
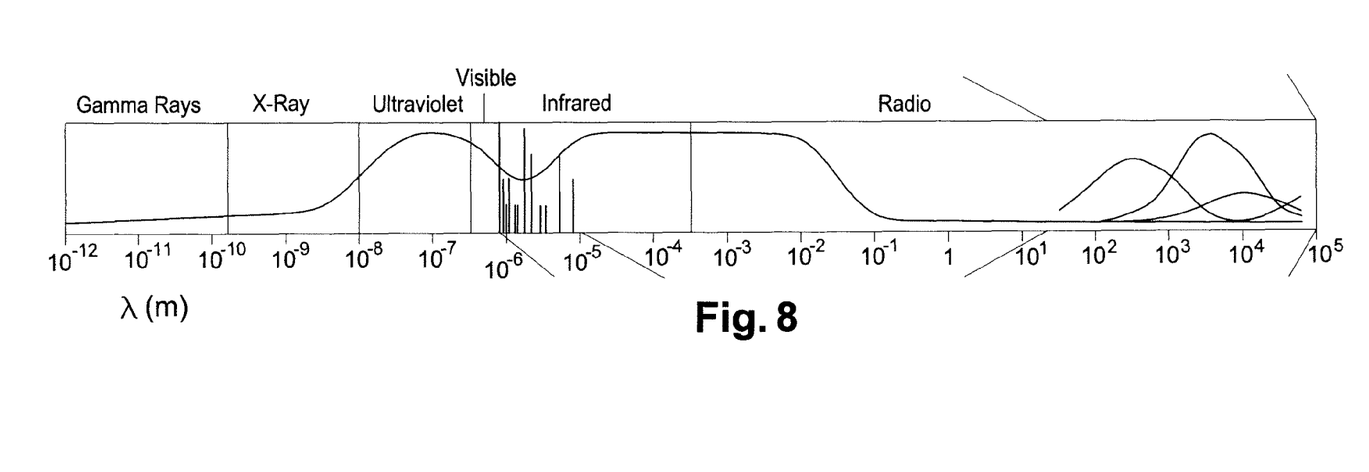

After numerous studies and tests, the applicant has noticed surprisingly a priori that some materials likely to form packages, glass in particular, have a wavelength window for which their radiation absorption coefficient drops notably. FIG. 8 in particular illustrates the evolution of the absorption coefficient for glass. It is evident from FIG. 8 that the coefficient of the glass drops substantially for the range of radiation applied between 0.7 µm and 3 µm. This particular range of wavelengths for which radiation can pass through the material constituting the package can be employed for analysing the content.

Figure 9A:
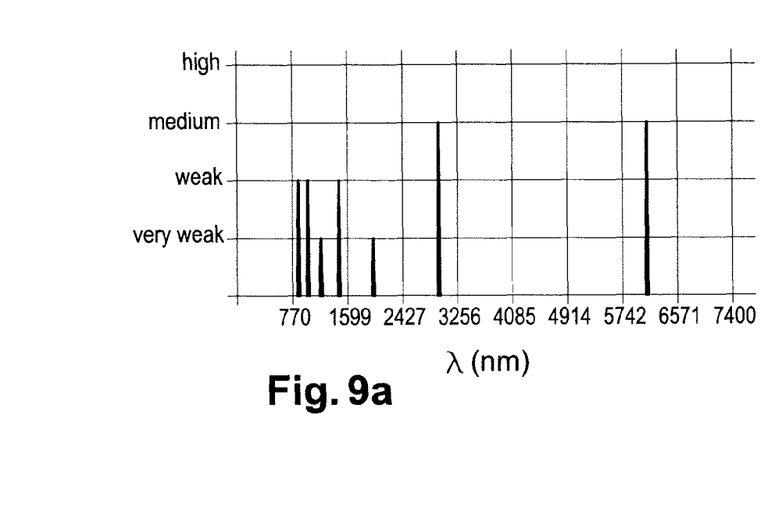
Figure 9B:
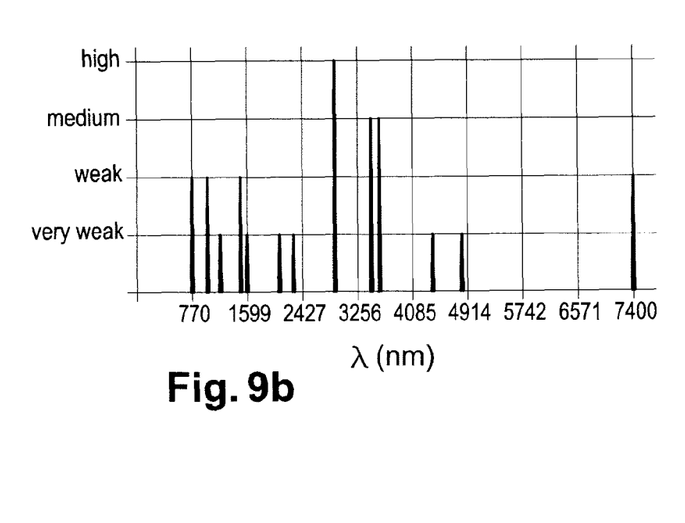

As will be explained hereinbelow, the invention actually distinguishes water-based liquids, and water in particular, from a strongly oxygenated liquid, hydrogen peroxide in particular, to the extent where these liquids have different absorption coefficients over a given range of wavelengths as illustrated in FIGS. 9a and 9b.

The present invention is also based on the following approach.

Dielectric materials have four base polarisations: electronic, ionic, dipolar and migrational.

Each type of polarisation is characterised by a positioning time, known as rise time. If the electromagnetic excitation field has a pulse greater than the inverse of the rise time, polarisation cannot take place. Consequently, polarisation is present only at frequencies less than those of cutting and is absent in greater frequencies. In the transition zone, there is an energy loss phenomenon in the dielectric due to rotation of the dephased molecules vis-à-vis the excitation field.

Rise times for electronic polarisation are from $10^{-14}$ to $10^{-15}$ seconds, in the optical field that is. Such a frequency range is difficult to exploit on an industrial scale as the bottles to be examined can frequently be partially or completely opaque.

Ionic polarisation has rise times of between $10^{-13}$ and $10^{-14}$ seconds, very close to the electronic relaxation time. It is thus also difficult to exploit.

Dipolar polarisation is characteristic of polar dielectrics (such as water for example).

Dipolar polarisation, contrary to electronic and ionic polarisations, which are without inertia, persists for a certain time after extinction of excitation. Dipolar polarisation diminishes with an exponential law and time constant, known as relaxation time, of between $10^{-6}$ and $10^{-11}$ seconds, that is, in the radio frequency range. Electromagnetic waves having these frequencies can pass through glass, plastic and other dielectric materials. The applicant has thus determined that electromagnetic waves can be utilised for examining the contents of bottles or equivalent containers.

Migrational polarisation is present in some dielectrics, in particular in heterogenic materials containing impurities. In this case, loads shift very slowly and the rise time can be several seconds, minutes, or even hours sometimes. This type of polarisation consequently is measurable at very low frequency only.

Figure 3:
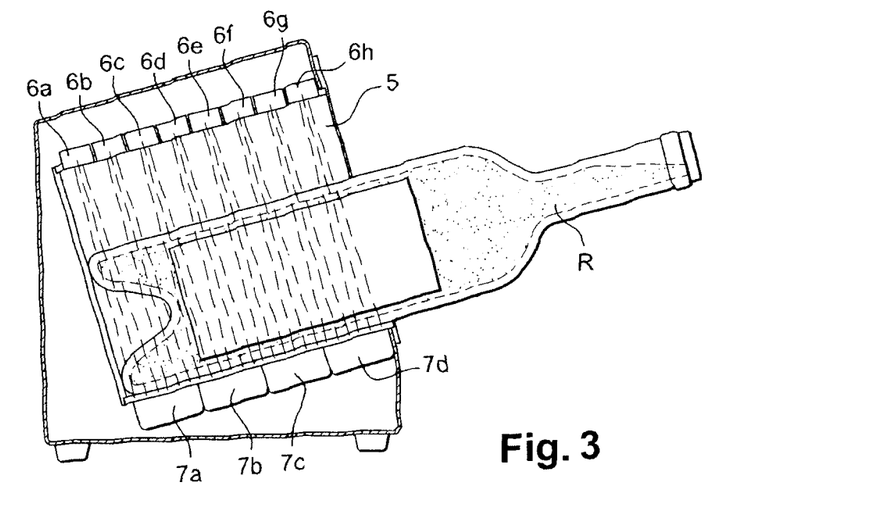

Water which is a polar liquid, and consequently water-based liquids, have a relaxation time of the order of $10^{-11}$ seconds at ambient temperature, corresponding to a frequency of around 16 GHz. Measuring the complex dielectric constant at lower frequency than that of relaxation shows a high real part and limited losses (distilled water) as illustrated in FIG. 3.

Saturated hydrocarbides $CnH(2n+2)$ are non-polar molecules or those with a very low electric dipole moment, consequently, they do not exhibit a dipolar polarisation phenomenon and the value of the real part of the constant dielectric is low (relative dielectric constant of the order of 2). Losses in hydrocarbides are negligible up to very high frequencies. If a hydrocarbide molecule loses its symmetry, such as for example in the case of ethylic or methylic alcohol, there is the appearance of an electric dipole moment and, consequently, a constant greater than that obtained in the case of hydrocarbides, and a resonance phenomenon with dipolar relaxation frequency.

The physical phenomena described hereinabove have been known since the late thirties (see for example Peter Debye Nobel Lecture, 1936).

However, to date they have not been used for efficacious analysis of the contents of containers.

Figure 1:
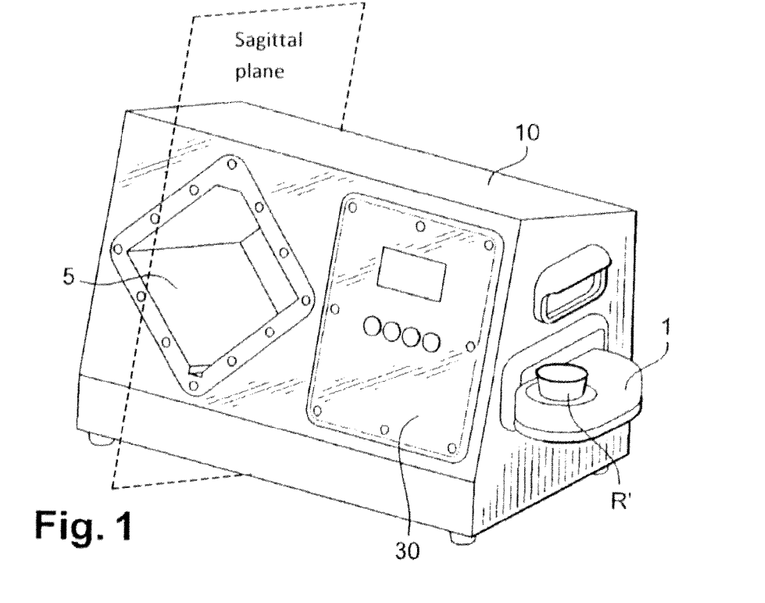
FIG. 1 illustrates a schematic view in perspective of an analysis device in keeping with a first embodiment of the present invention.

FIG. 1 illustrates the case of an analysis device according to the present invention.

The general geometry of this case can be the object of numerous variant embodiments and thus will not be described in detail hereinbelow.

This case preferably comprises a metallic housing 10 for forming shielding around the electromagnetic sensor according to the present invention vis-à-vis the external environment.

This housing preferably defines a cavity 5 whereof the lower part 22 has a concavity pointing upwards, designed to receive a container to be analysed and guarantee precise positioning of the latter relative to the transmitter/receiver means of electromagnetic field according to the invention.

Still more precisely, preferably, within the scope of the present invention the abovementioned cavity 5 is preferably formed by a channel of constant cross-section whereof the generators are inclined down as they move away from the open front face 12 via which a container is introduced.

The rear face of this cavity or channel 5 is preferably closed to prevent the analysed container from slipping on the base 22.

The cross-section of the channel 5 can be the object of numerous variants. FIG. 1 illustrates a first variant according to which the channel 5 has a square cross-section.

The cavity 5 can of course have other forms. For example, in an embodiment, the channel 5 has a circular cross-section. In another variant embodiment the channel 5 has a cross-section in the form of a keyhole comprising a cylindrical central part prolonged by two diametrically opposed bulges of overall rectangular contour. In yet another embodiment, the channel 5 comprises a cross-section of rectangular form, whereof the diagonals are respectively vertical and horizontal such that a ridge coincides with the lowest point of the channel 5. The advantages of the different variants of cross-sections will be explained hereinbelow.

The case 10 further preferably includes a control console 30 equipped with an acquisition and/or programming keyboard, a display and signalling means (light and/or sound) for presence of network and alarm. In this respect, the invention is of course not limited to the particular embodiments illustrated in the attached figures.

The cavity 5 is preferably coated by a protective plastic coating.

The device according to the invention comprises spectral analysis means 6, 7 to allow detection of liquids, which when blended, can produce a dangerous substance (explosive, producing toxic fumes, etc.).

Figure 2:
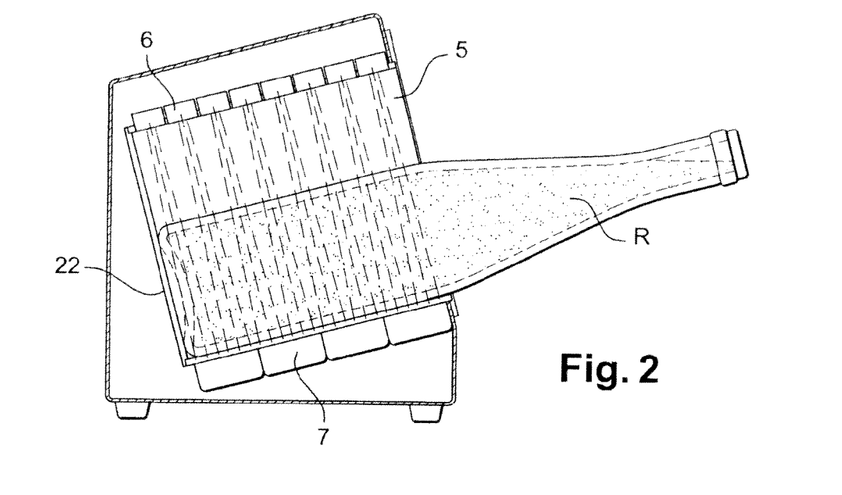
FIGS. 2 to 4 illustrate schematic views in section of the device of FIG. 1.

These spectral analysis means 6, 7 are illustrated especially in FIG. 2. The spectral analysis means 6, 7 measure wave absorption of the container R and its contents.

Advantageously, the spectral analysis means 6, 7 are suitable for sending waves whereof the wavelengths are in the infrared spectrum, and for measuring the absorption of these waves by the container and its contents.

This spectral analysis is conducted through the walls of the container R.

Infrared radiation is preferably emitted by the spectral analysis means 6, 7 at wavelengths between 0.7 µm and 3 µm.

In fact, the advantage of infrared radiation of wavelengths between 0.7 µm and 3 µm is that they pass through glass containers especially, even if they are opaque or coloured. Also, with infrared waves, the wave absorption of the walls of the container R is negligible relative to the wave absorption by the liquid contents in the container R.

Accordingly, such spectral analysis is influenced only slightly by the walls of the container R, and measuring wave absorption corresponds substantially to the wave absorption of the liquid contents in the container R.

As mentioned hereinabove, the invention distinguishes water-based liquids, and in particular water, from strongly oxygenated liquid, in particular hydrogen peroxide, to the extent where as illustrated in FIGS. 9a and 9b these liquids exhibit different absorption coefficients over a given range of wavelengths.

In a preferred embodiment, the analysis means are suitable for sending waves whereof the wavelength is between 1000 nm and 1400 nm. In fact, it has been discovered that in the wavelength range between 1000 and 1400 nm, the colour of glass constituting the bottles of wine or other alcohols have a minimal percentage of wave absorption by comparison with water.

In fact, the water molecule has an absorption peak in this range. The fact of working on an absorption peak of water might seem disadvantageous, since radiation attenuation is very pronounced. However, the fact that water absorption is predominant in this wavelength band (i.e. 1000 nm-1400 nm) relative to the absorption of the container allows independent measuring of the material comprising the container, in particular when this container is made of dark glass or opaque plastic.

When working at the absorption peak of water, measuring is no longer dependent on the selectivity of the container but is especially sensible to the liquid itself.

In other terms, the wavelength band between 1000 nm and 1400 nm offers good independence vis-à-vis the material constituting the container containing the liquid to be analysed.

The spectral analysis means 6, 7 can comprise one or more transmitters 6 for the emission of infrared waves, and one or more receivers 7 for reception of waves emitted which have passed through the container R and its contents.

Each transmitter 6 can be associated with one or more receivers 7. Similarly, each receiver 7 can be associated with one or more transmitters 6.

In the embodiment illustrated in FIG. 2, the spectral analysis means 6, 7 comprise eight transmitters 6 and four receivers 7, each receiver 7 being associated with two transmitters 6.

The transmitters 6 and receivers 7 are placed in the sagittal plane of the channel 5 to the right of one another, such that the waves emitted by the transmitters 6 pass through the container R and its contents prior to being received by the receivers 7.

More precisely, the transmitters 6 are placed on the channel 5 and the receivers 7 are placed under the channel 5. Placing the transmitters 6 on the channel 5 avoids the risks of blinding the user, the infrared beam being sent from high to low.

Nevertheless, other configurations are feasible. For example, in another embodiment, transmitters 6 and receivers 7 are placed in the median plane of the channel 5 opposite one another, such that the waves emitted by the transmitters 6 pass through the container and its contents prior to being received by the receivers 7.

The fact that the analysis device according to the invention comprises an inclined cavity for receiving the container whereof the contents have to be analysed permits precise and repeatable positioning of the container relative to the transmitters 6 and receivers 7 of the device.

Also, placing the receivers 7 under the cavity 5 limits the effects of ambient light in order to improve measuring precision. In fact, when the container whereof the contents have to be analysed is placed in the cavity 5, the receivers 7 are covered by the container such that the body of the container prevents ambient radiation from being received by the receiver, ambient radiation which can perturb analysis.

In yet another embodiment, the transmitters 6 are placed in the sagittal plane of the channel 5, said transmitters 6 being alternatively placed on and under the channel 5, and being associated with receivers 7 placed to the right of said transmitters 6.

The operating principle of the device according to the invention is the following. As illustrated in FIG. 3, during analysis the transmitters 6 emit infrared waves. These infrared waves pass through the walls of the container R and the liquid contents in the container R, the liquid absorbing the different waves emitted by the transmitters 6 as a function of its nature. The waves not absorbed (or having been partially absorbed) are then received by the receivers 7.

Measuring the relative absorption for two, three or more correctly selected wavelengths defines whether the liquid contents in the container R, even if belonging to the class of homopolar liquids such as water, is in reality potentially dangerous.

In parallel or sequentially, measuring the complex impedance of the container and its contents (the principle of which will be mentioned hereinbelow) determines whether the liquid contents in the container are an inflammable or explosive liquid.

As illustrated in FIG. 3, the transmitters 6 and receivers 7 can be placed along the channel 5, the receivers 7 being placed so as to receive the waves emitted by the transmitters 6.

This produces measuring of the absorption of the container R and its contents even if the container R comprises a hollow base, or if the container R comprises a label blocking the passage of infrared waves through its walls over a portion of its surface contained in the channel 5.

For example, when the container R comprises a hollow base, only the infrared waves emitted by some of the transmitters placed between the opening of the channel 5 and the base of the channel 5 will pass through the container R and its contents. Spectral analysis will in this case be based solely on the waves having passed through the container and its contents.

In the case illustrated in FIG. 3, only the waves emitted by the transmitters $6c$ to $6h$—which are the closest transmitters to the opening of the channel 5 among the eight transmitters $6a$ to $6h$—and received by the receivers $7b$ to $7d$ will be taken into account for spectral analysis.

Figure 4:
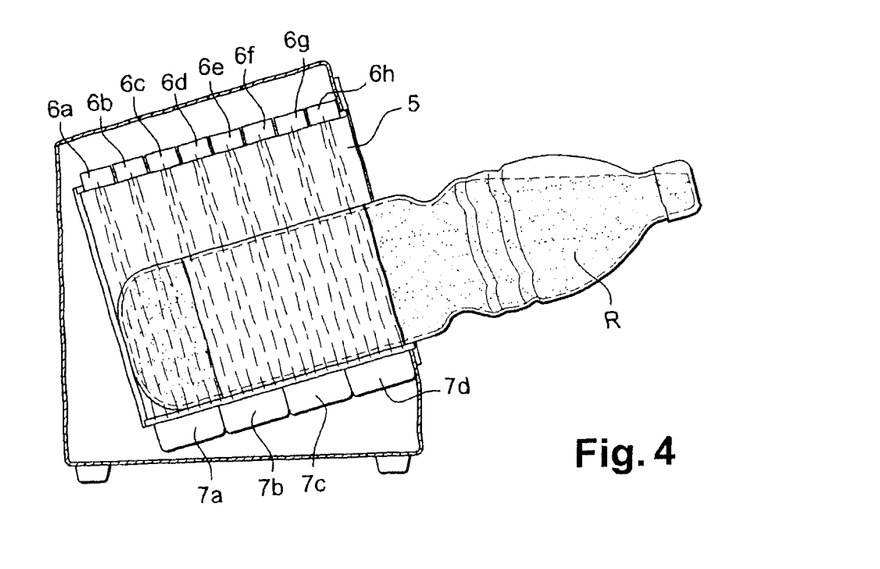

In the case illustrated in FIG. 4, only the waves emitted by the transmitters $6a$ and $6b$—which are the closest transmitters to the base 22 of the channel 5—and received by the receiver $7a$ will be taken into account for spectral analysis, the infrared waves emitted by the transmitters $6c$ to $6h$—the farthest from the base of the channel 5—being blocked by a label located on a portion of the container R, over its entire circumference.

Advantageously, the analysis device can comprise control means for automatically finding, by electronic scanning (scanning), the position(s) where light attenuation is minimal between transmitter and receiver, thus the transmitter/receiver couple(s) produce the most precise measuring.

With the analysis device according to the invention, it is accordingly unnecessary for the user to manually position the transmitters and the receivers to avoid labels. The analysis device according to the invention thus enables rapid, precise and easily repeatable analysis of liquids contained in containers.

Using spectral analysis means 6, 7, especially infrared, produces very useful data for characterising the nature of liquid contents in a container R, and automates analysis of the contents of the container R without the need for intervention by the user.

If the material of the container R is totally opaque to infrared, it can be possible to employ means described hereinbelow, with or without intervention of the user for intercepting additional data on the nature of a container and/or its contents.

Advantageously, the device described earlier can be used in combination with the device described in document EP 1 712 900 for measuring the complex impedance of the container and its contents and which is described hereinbelow.

Figure 5:
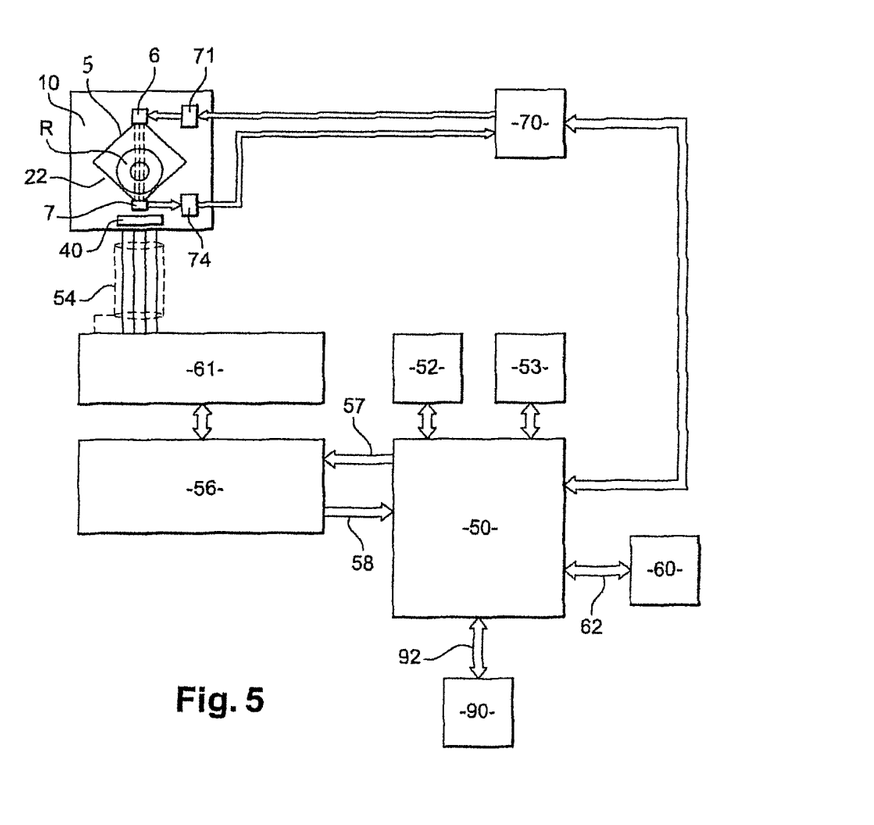
FIG. 5 illustrates a schematic view in the form of functional blocks of elements comprising the device of FIG. 1.

As illustrated in FIG. 5, showing a container to be analysed under reference R and showing the base 22 of the cavity 5, preferably an electromagnetic sensor or sensors designed to measure the complex dielectric characteristics of the bottle R and its contents are placed around the cavity 5.

These electromagnetic field transmitter/receiver means are preferably formed by one or more transducers (antennae) 40 connected by means of a connection network 54, an electromagnetic measuring network 56 and bus network 57, 58, to a generator designed to send an electromagnetic wave. Typically the generator is adapted to cover the frequency range from a few Hz, for example 5 Hz to a few GHz, for example 5 or 50 GHz. The generator is operated, either manually by an operator when the latter introduces a container R to the channel 5, or automatically under the effect of a sensor 52 designed to detect the presence of a container R in the channel 5.

Means 50 are designed for measuring the complex impedance of the transmitter means 40 influenced by the load constituted by the container R and its contents, representative of the complex dielectric characteristics of this container R and its contents. More precisely, the means 50 are designed for measuring this complex impedance at several tiered frequencies over the abovementioned excitation range of a few Hz to several GHz. Typically, the means 50 operate on a number of frequencies between 10 and 50, advantageously on thirty frequencies.

The device also comprises:
infrared radiation transmitters 6 placed in the sagittal plane of the channel 5, above the latter and
infrared radiation receivers 7 placed in the sagittal plane of the channel 5, below the latter.

A spectral analysis system 70 is adapted for measuring the absorption of infrared radiation by the container R and its contents. The spectral analysis system 70 is connected to the transmitters 6 by means of a control module 71 of the radiation transmitters 6 and to the receivers 7 by means of a control module 74 of the radiation receivers 7.

The means 50 are adapted to provide information connected to the nature of the contents of the container detected as a function of the complex measured impedance and of the measure of the absorption.

These means 50 are preferably adapted for comparing the complex measured impedance and the absorption measuring with predetermined reference values stored in a memory 60 and are adapted for generating an alarm when the complex measured impedance and/or the absorption measuring moves away from the reference values.

FIG. 5 illustrates a memory 60 coupled to analysis means 50 by a communications bus 62, and in which the predetermined reference values on the work frequency range for the complex impedance and on a work wavelength range for the absorption measuring can be stored. Under the reference 90, the same FIG. 5 also illustrates alarm means, present preferably on the control console 30, connected to the means 50 by a communications bus 92 and adapted to generate a sound and/or visual alarm, when the complex measured impedance moves away from the reference values.

As a variant, the reference values can be calculated by the means 50 and not contained in a memory 60.

Also, according to another variant, the means 90 can be adapted to directly indicate the nature of the contents of the container R or at least the family of these contents at the place of or as complement to the abovementioned alarm means.

The electromagnetic field transmitter/receiver means 40 can be the object of numerous embodiments.

The means 40 can be formed by a simple spool forming transmitter and receiver, connected by a dual-wire network to the means 56.

The means 40 can also be formed by two spools forming respectively, and if required alternatively, transmitter and receiver, connected by a four-wire network to the means 56.

The means 40 can also be formed by two armatures of a capacitance surrounding the cavity 5 for receiving the container R and connected by a dual-wire network to the means 56.

The means 40 can comprise (two) six crossed capacitances composed of four armatures connected by a four-wire network to the means 56 and forming respectively, and if required alternatively, transmitter and receiver.

The means 40 can be formed by transmission lines. Typically, these transmission lines operate in the microwave range. They can be formed by dual-wire lines or slotted wave guides.

Also, within the scope of the present invention, sensors can be used which simultaneously employ an inductive transducer and a capacitive transducer. This arrangement detects that the growth of the real part of the complex dielectric constant is due to a metallic armature internal to the container and not to a liquid or liquids having particular properties. This arrangement thus detects the presence of metallic screens suitable for forming shielding perturbing measuring. The inductive sensor fed by an alternative current source will in this case produce Foucault currents in the metallic part. These currents will be measured by the processing device. And comparison of the signals coming from the electric field transducer and from the magnetic field transducer 42 enables satisfactory detection.

Of course, the number of means comprising the transmitters and/or receivers is definitely not limited.

The expert will understand from reading the preceding detailed description that the present invention proposes an electromagnetic sensor for scanning high frequencies which measures the dielectric characteristics of the bottle R and its contents.

As described previously, the cross-section of the channel 5 can be the object of numerous variants. For example, the cross-section can be in the form of a keyhole, the cross-section can also be circular in shape, or square or even rectangular (with vertical and horizontal diagonals).

For some geometries of the cross-section of the channel, the complex measured impedance can vary as a function of the volume of the container in which the same analysed liquid is contained.

Accordingly, in the case of a channel 5 whereof the cross-section is circular in shape, the complex measured impedance Zmeasured for a container R of 50 centiliters containing water (FIG. 12a) will be different to the complex measured impedance Zmeasured for a container R of 2 liters containing water (FIG. 12b).

This is because of the fact that the Zmeasured complex measured impedance corresponds to the Zequivalent complex impedance equivalent of all the dipoles located between the armatures of the electromagnetic field transmitter/receiver means.

The Zmeasured complex measured impedance is thus equal to the sum of the complex impedance of water Z2 contained in the container R and the complex impedances Z1 and Z3 of the air situated between the walls of the container R and the armatures.

The complex impedances Z1 and Z3 of the air situated between the walls of the container R and the armatures are considered as parasite impedances to be minimised so that the complex measured impedance is substantially equal to the complex impedance of the liquid contents in the container to be analysed.

The square/rectangular geometries (whereof the diagonals are respectively vertical and horizontal such that a ridge coincides with the lowest point of the channel 5) and in a keyhole of the cross-section has the advantage of making measuring the complex impedance independent of the volume of the container in which the liquid to be analysed is contained.

In fact, these geometries limit the distance between the walls of the container R and the armatures of the electromagnetic field transmitter/receiver means, irrespective of the volume of the container R.

In the case of a container R of cylindrical shape placed in a channel 5 of square cross-section, the container R will have a tendency to come into contact with the partitions of the channel 5 due to gravity.

Accordingly, the distance between the walls of the container and the armatures (which are very close to the partitions of the channel 5) is virtually zero irrespective of the diameter of the container containing the liquid to be analysed, such that the parasite impedances Z1 and Z3 of the air situated between the walls of the container R and the armatures are negligible. The Zmeasured measured impedance is substantially equal to the complex impedance of the liquid contents in the container R irrespective of the volume of the container R utilised.

As for a channel whereof the cross-section is square, a geometry of cross-section in a keyhole form minimises the distance between the walls of the container containing the liquid to be analysed and the armatures of the device, irrespective of the volume of the container R utilised, such that measuring the complex impedance is independent of the volume of the container in which the liquid to be analysed is contained. Accordingly, in the case of a cylindrical container of 50 cl, the latter is positioned between the lower bulges of the cross-section in keyhole form (the distance between these bulges can be provided slightly larger than the diameter of a cylindrical bottle of 50 centiliters of standard type). In the case of a container of 2 liters, the latter is positioned at the level of the central cylindrical part of the channel in keyhole form.

Accordingly, the channel 5 of the device preferably defines a concavity 22 pointing upwards. Even more preferably, convergence of the partitions 86, 87 of the channel 5 is determined such that not only does the distance between the lowest point of the channel 5 and the centre of gravity of the container R increase as a function of the volume of the container R but also the point of contact of the container R on the walls of the channel 5 rises and the height of the base of the container relative to the lowest point of the channel 5 also increases as a function of the volume of the container R. More preferably still, the upwards pointing concavity is produced due to two rectilinear sections so as to minimise the effect of the parasite impedances Z1 and Z3 of the air situated between the walls of the container R and the partitions of the channel 5.

The device described previously has non-destructive investigation means for determining the composition of the contents of a container.

To improve reliability of the analysis device, means 53 for producing an additional physical data relative to a characteristic of the container analysed can be integrated into this device.

In a variant of the invention, the means for producing an additional physical data comprise means for measuring the mass of the container R analysed.

In fact, when the capacity of the container analysed is low (i.e. under 200 mL), the device described previously tends to underestimate the complex impedance of the liquid contents in the container analysed, which can lead to a false alarm being given.

More precisely, the complex impedance for a unit of volume of liquid measured in a container of 100 mL capacity for example will be less than the complex impedance for a unit of volume of the same liquid measured in a 2 L container.

The same applies when a container of square shape is placed in a channel of square cross-section. More precisely, the complex measured impedance of liquid contents in a container of square cross-section of 1 L will be greater than the complex measured impedance of the same liquid contents in a cylindrical container.

This is due to the fact that in both cases, the walls of the container (of square cross-section, or minimal capacity) cooperate differently with the walls of the channel.

To increase the reliability of the device described previously, it is thus proposed to procure for the analysis means 50 an additional data in addition to the complex measured impedance and measurement of the wave absorptions.

This additional data is the mass of the container, and preferably of the container with its contents.

To measure the mass of the container and of the liquid it contains, the device comprises a gravimetric sensor 53.

Preferably, the gravimetric sensor 53 is placed integrated with the channel 5.

More precisely, the gravimetric sensor 53 is placed under the lower part (or base 22) of the channel 5. This effectively limits the bulk of the device.

The device operates as follows.

The tare of the device is measured periodically. More precisely, when no container is introduced to the channel 5, the gravimetric sensor 53 measures the mass of the lower part 22 of the channel 5. This measured tare is sent to the means 50.

The presence of a container in the channel 5 is detected:
either by the sensor 52,
or by the means 50.

In the event where the presence of a container is detected by the means 50, this detection is done as follows. The user introduces a container on the lower part 22 of the channel 5. The complex impedance of the transmitter/receiver means is influenced by the load constituted by the container R and its contents. The analysis means 50 detect this modification of complex impedance and send a signal indicating the presence of a container to be analysed to interrupt periodical updating of the tare of the device.

The gravimetric sensor 53 measures the mass of the container R and its contents and sends a signal representative of the measured mass to the analysis means 50.

The analysis means 50 associate the measured mass with the complex measured impedance for the analysed container R.

More precisely, the measured mass is used to correct the amplitude of the complex measured impedance.

The complex impedance thus corrected is then compared to reference values.

In another variant of the invention, the means producing an additional physical data comprise acquiring means 55 illustrated in FIGS. 2 and 14.

The acquiring means 55 can allow detection of additional data relative to the analysed container.

Because of these additional data, the selectivity of the device can be augmented.

In fact, the knowledge of additional data reduces the window of acceptance on the complex measured impedance. Without additional data the window of acceptance has to be wide enough to consider the variability of physical factors relative to the different types of container suitable to be analysed, such as:
the material constituting the walls of the container,
the thickness of the walls of the container,
the capacity (or volume) of the container.

The device can thus comprise acquiring means 55 for acquiring additional data relative to the analysed container.

To make it easier to use the device, the analysis means 50 propose questions displayed on display means 59, as well as a list of possible responses.

Due to acquisition means 55, the user selects, as a function of the analysed container, the most appropriate response from the list of proposed responses.

The additional data which the user has to acquire can be the capacity (i.e. volume) of the container and/or the material constituting the walls of the container and/or the thickness of the walls of the container.

Advantageously, the analysis means 50 display questions relative to the analysed container only when acquisition of additional data relative to the analysed container is necessary to determine the nature of the liquid contents in the analysed container.

In this case, the means 50 furnish information relative to the nature of the contents of the container as a function of the complex measured impedance and of the data or data acquired by the user on the acquiring means 55.

For example, when the complex measured impedance moves away from the reference values, the analysis means 50 command the user (via display means 59) to acquire additional data on the acquiring means 55.

In yet another variant, the means producing an additional physical data comprise means for measuring both the mass and acquiring means.

Measurements of the complex impedance and of the wave absorptions (with or without additional data) can be taken sequentially—due to a commutation block 61—or in parallel. In the event where measurements of the complex impedance and of the wave absorption are taken sequentially, the complex impedance can be measured before or after measuring the infrared wave absorptions.

An example of analysis sequence can be the following:
i) manual insertion of the container and its contents in the channel 5, ensuring inserting it as far as the base 22 of the channel 5, the bottle being placed such that the label (in the case of a label not covering the entire circumference of the container) is not in the radiation zone situated between the transmitters 6 and the receivers 7,
ii) execution of measuring the complex impedance by the means 50 due to the electromagnetic measuring network 56 and the commutation block 61, and recording of the measurement in the memory 60,
iii) in the event where measuring complex impedance reveals the presence of inflammable or explosive liquid in the container, the alarm means 90 generate a sound and/or visual alarm, if not, spectrometric analysis is conducted by the spectral analysis system 70 and the various elements 71, 6, 7, 74 of the spectral analysis means,
iv) in the event where the result of the spectral analysis confirms the presence of a potentially dangerous liquid when mixed with other dangerous liquids to produce an explosive, toxic, etc. substance, the alarm means 90 generate a sound and/or visual alarm.

In the event where the container R is totally opaque to infrared radiation and/or electromagnetic waves for measuring the complex impedance, a secondary analysis device 1 can be provided in addition to the main analysis device described previously.

The secondary analysis device enables both:
measurement of the complex impedance, and
measurement of the wave absorption.

Figure 6:
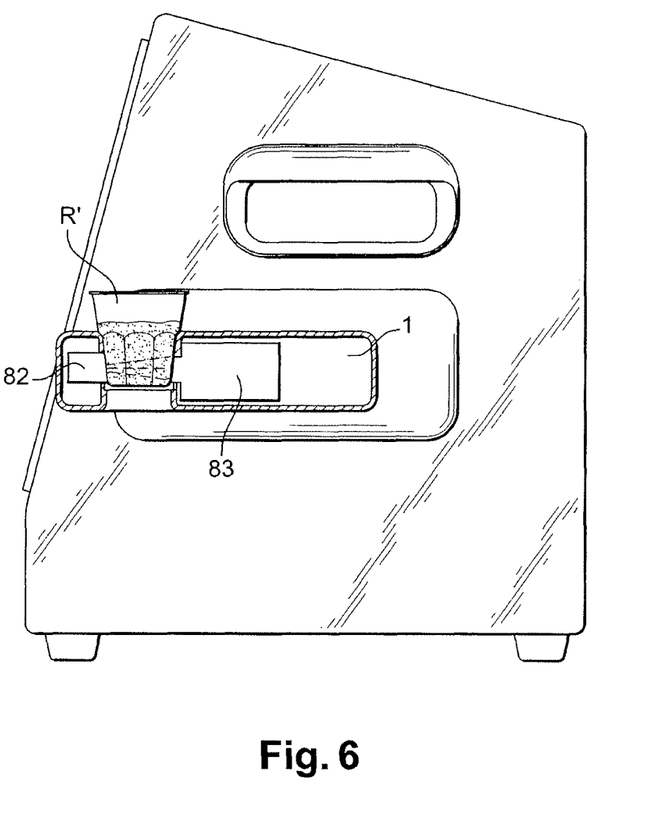
FIG. 6 illustrates a schematic side view of a portion of an analysis device in keeping with a second embodiment.

FIG. 6 illustrates such a secondary analysis device.

The secondary analysis device comprises:
secondary transmitters/receivers means 40' of an electromagnetic field,
a secondary container R' for receiving contents to be analysed,
secondary support means 22' of the secondary container R',
secondary spectral analysis means.

Using an identical secondary container R' for each analysis ensures constant positioning between the secondary transmitter/receiver means and the secondary container R'. Ensuring constant positioning of the secondary container R' eliminates one of the variables of analysis, specifically the variability of positioning the container containing the liquid to be analysed relative to the transmitter/receiver means.

The secondary container R' is preferably designed to accommodate a constant volume of liquid. The dimensions of the secondary container R' are for example such that they hold a constant volume of liquid between 2 and 10 centiliters.

Also, the thickness of the walls of the secondary container R' can be constant.

Using identical containers for all analyses increases the reliability of the device and reduces the acceptance window on the complex measured impedance.

Without constancy on the container used for analysis, the acceptance window has to be wide enough to consider the variability of physical factors relative to the different types of container to be analysed.

These physical factors are for example:
the material constituting the walls of the container,
the thickness of the walls of the container,
the capacity (or volume) of the container.

The secondary support means 22' are specially adapted to supporting the secondary container R'.

Preferably, the dimensions of the secondary support means 22' are such as to cooperate closely with the walls of the secondary container R'.

Also, the secondary support means 22' are such that, when in use, the secondary support means 22' surround the walls of the secondary container R'.

The spectral analysis and measuring means of the complex impedance of the main and secondary devices operate on the same principle.

Figure 7:
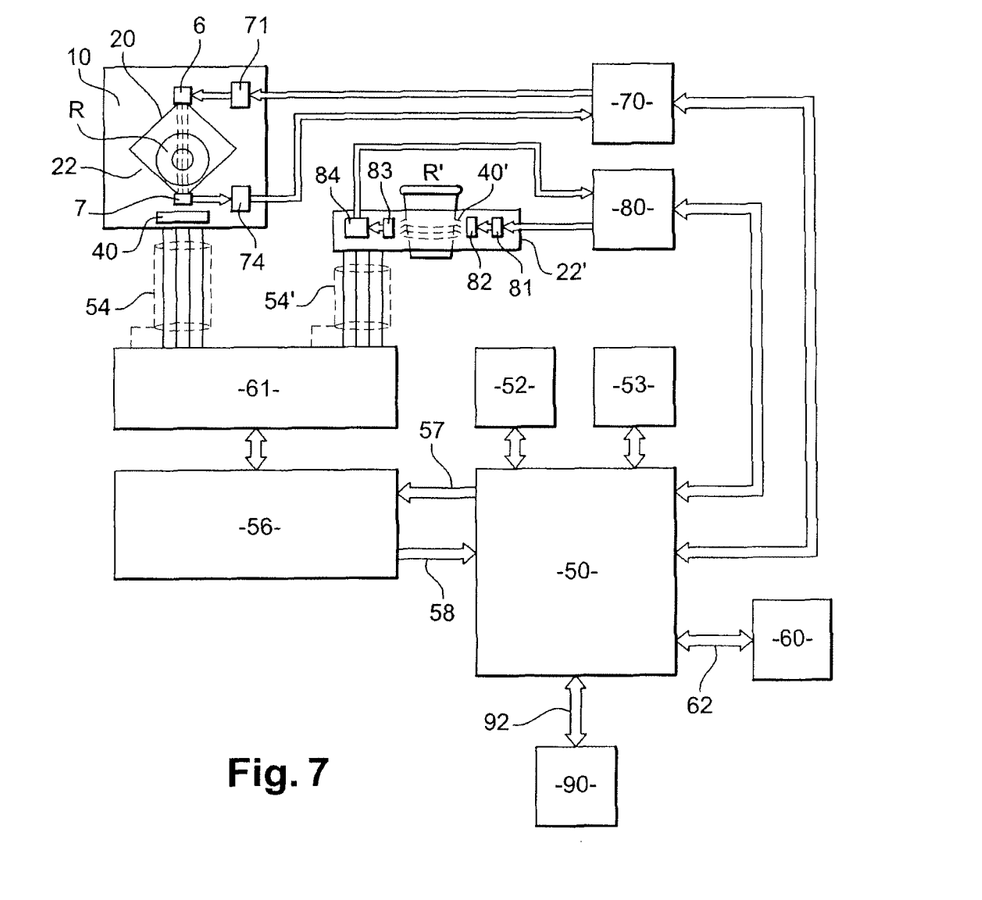
FIG. 7 illustrates a schematic view in the form of functional blocks of elements comprising the device in keeping with the second embodiment, FIG. 8 schematically illustrates the evolution of the absorption coefficient of the glass as a function of the wavelength of applied radiation, and FIGS. 9a and 9b schematically illustrate the absorption coefficients of a liquid based both on water and a strongly oxygenated liquid, such as hydrogen peroxide ($H_2O_2$), for a range of radiation wavelengths.

The secondary spectral analysis means comprise secondary transmitters 82 connected to a secondary spectral analysis system 80 via a secondary control module of the transmitters 81, and secondary receivers 83 connected to the spectral analysis system secondary 80 by means of an amplification module 84 for pre-processing the analog data coming from the secondary receivers 83.

Advantageously, some elements of the spectral analysis and measuring means of the complex impedance can be common to the main device and to the secondary device.

The secondary transmitter receiver 40' means are preferably formed from one or more core spools forming an antenna, connected by means of a connecting network 54' of an electromagnetic measuring network 56 and bus network 57, 58 to a generator 50, designed for sending an electromagnetic wave.

The present invention is naturally not limited to the particular embodiments which have just been described, but extends to any variant in keeping with its central idea.

It is also evident, within the scope of the present invention, that the sensors 40 are preferably adapted to cover at least a substantial part of the containers, or even all of them, guaranteeing a high level of security in analysis, since this permits analysis of all the contents of the containers and not only part thereof.

When a single transducer is provided, the latter is simultaneously or successively transmitter and receiver.

When several transducers are provided, all combinations are possible, that is, these transducers can be simultaneously or successively transmitter and/or receiver.

According to another advantageous characteristic, the analysis device according to the present invention also comprises an ionising or radioactive radiation detector assembly. This assembly is intended to detect the possible presence of traces of radioactive products in the analysed container.

The ionising or radioactive radiation detector assembly can be the object of numerous embodiments. It can be formed from all structures known to the expert, in particular any structure suitable for converting a detected ionising beam into a useable electric signal. It can be for example and not limiting a Geiger-type detector comprising a tube or chamber housing a gas whereof the composition is selected to generate an ionising discharge during detection of active radiation, and from there an electric pulse. It can also be a scintillator detector suitable for converting the energy detected into light scintillations then converted into an electric signal by a network of photomultiplies. Numerous scintillators have been proposed to this effect, for example those based on sodium iodide, caesium iodide or even bismuth germanate.

The ionising radiation detector assembly is placed in any appropriate place and preferably in the immediate proximity of the walls of the cavity 5, on the exterior thereof. FIG. 8, under the reference 100, 110, illustrates optimal localisation a priori of this assembly, under the cavity 5, against the two walls comprising the lower dihedral of the cavity 5.

The ionising radiation detector assembly 100, 110 is adapted to work in masked time, in parallel with the complex impedance measuring device previously described. The ionising radiation detector assembly 100, 110 is controlled and placed into service by any appropriate means detecting the presence of a container in the cavity. The ionising radiation detector assembly is preferably, but not limitingly, thus initiated by a signal taken on the complex impedance measuring chain and representative of the presence of such a container in the channel 5.

Several embodiments of means 40 forming electromagnetic field transmitters/receivers have been described earlier. Within the scope of the present invention, means are preferably provided for modifying the configuration of the means forming transmitters and means forming receivers to enrich available information, for example on the volume of the analysed container.

Also, the reader will appreciate that the device according to the invention is not limited to emission of radiation in the infrared spectrum. For example, the transmitter or transmitters can send out radiation in the ultra-violet spectrum, or in the visible light spectrum.

The invention claimed is:

1. A device for analyzing the composition of the contents of containers having different shapes, the device comprising:
   a channel configured to receive said differently shaped containers, the contents of which are to be analyzed, said channel having a lower part which has a concavity pointing upwards, being inclined downward away from an open front face through which one of said containers is introduced and having a closed rear face, and
   a spectral analyzer for transmitting and analyzing waves in the infrared spectrum, said spectral analyzer being configured to measure the absorption of said waves by the introduced container and its contents, said spectral analyzer including a plurality of transmitters configured to transmit said waves and a plurality of corresponding receivers configured to receive said transmitted waves, each receiver placed so as to receive the waves emitted by its corresponding transmitter, wherein each of said plurality of transmitters is placed on the channel, and each of said plurality of receivers is placed under the channel, wherein a sagittal plane passes through each of said transmitter receiver pairs such that the infrared wave emitted by each transmitter passes through said introduced container and its contents prior to being received by the corresponding receiver, said plurality of transmitters and receivers enabling said spectral analyzer to perform a spectral analysis of the contents of said introduced container, said spectral analyzer further comprising control means for automatically selecting, by electronic scanning, the transmitter and receiver pair having the least amount of light attenuation caused by a label on said introduced container positioned to block some of the infrared waves emitted by said infrared wave transmitters, and
   at least one of an audio and visual mechanism configured to provide information concerning the nature of the contents of said containers as a function of the wave absorption measuring.

2. The device as claimed in claim 1, wherein the wavelengths of the waves being transmitted are between 0.7 μm and 3 μm.

3. The device claimed as in claim 2, wherein the wavelengths of the waves being transmitted are between 1000 nm and 1400 nm.

4. A device for analyzing the composition of unknown contents of containers having different shapes, the device comprising:
   a channel configured to receive said differently shaped containers, the contents of which are to be analyzed, said channel having a lower part which has a concavity pointing upwards, being inclined downward away from an open front face through which one of said containers is introduced and having a closed rear face, and
   a spectral analyzer for transmitting and analyzing waves in the infrared spectrum, said spectral analyser being configured to measure the absorption of said waves by the introduced container and its contents, said spectral analyzer including a plurality of transmitters configured to transmit said waves and a plurality of corresponding receivers configured to receive said transmitted waves, each receiver placed so as to receive the waves emitted by its corresponding transmitter, wherein each of said plurality of transmitters is placed on the channel, and each of said plurality of receivers is placed under the channel, wherein a sagittal plane passes through each of said transmitter receiver pairs such that the infrared wave emitted by each transmitter passes through said introduced container and its contents prior to being received by the corresponding receiver, said plurality of transmitters and receivers enabling said spectral analyzer to perform a spectral analysis of the contents of said introduced container, said spectral analyzer further comprising control means for automatically selecting, by electronic scanning, the transmitter and receiver pair having the least amount of light attenuation caused by a label on said introduced container positioned to block some of the infrared waves emitted by said infrared wave transmitters, and
   at least one of an audio and visual mechanism configured to provide information to enable detection of dangerous substances within the contents of said introduced container as a function of the wave absorption measuring.

5. A device for analyzing the composition of the contents of a container, the device comprising:
   a channel configured to receive a container the contents of which are to be analyzed, wherein from a side view the channel has a closed rear, an open front, a top and a bottom, and a cavity defined within the channel, the channel being inclined so that the open front is higher than the closed rear and the container is introduced into the cavity through the open front; and a spectral analyzer for transmitting and analyzing waves in the infrared spectrum, said spectral analyzer being configured to measure the absorption of said waves by the introduced container and its contents, said spectral analyzer including a plurality of transmitters configured to transmit said waves and a plurality of corresponding receivers configured to receive said transmitted waves, each receiver placed so as to receive the waves emitted by its corresponding transmitter, wherein each of said plurality of transmitters is placed along the top of the channel, and each of said plurality of receivers is placed along the bottom of the channel, wherein a sagittal plane passes through each of said transmitter receiver pairs such that the infrared wave emitted by each transmitter passes through said introduced container and its contents prior to being received by the corresponding receiver, said plurality of transmitters and receivers enabling said spectral analyzer to perform a spectral analysis of the contents of said introduced container, said spectral analyzer further comprising control means for automatically selecting, by electronic scanning, the transmitter and receiver pair having the least amount of light attenuation that is caused by a label on said introduced container upon some of the waves emitted by said transmitters, and at least one of an audio and visual mechanism configured to provide information concerning the nature of the contents of said container as a function of the wave absorption measuring.

6. The device as claimed in claim 1, wherein said device further comprises at least one antenna for transmitting and receiving an electromagnetic signal with at least several frequencies in the range of 5 Hz to 50 GHz, at least one sensor configured to measure a complex impedance by the at least one sensor influenced by the load constituted by the introduced container and its contents, representative of complex dielectric characteristics of the introduced container and its contents using said electromagnetic signal, and wherein said at least one of an audio and visual mechanism is also configured to provide information concerning the nature of the contents of said containers as a function of the complex measured impedance.

7. The device as claimed in claim 4, wherein said device further comprises at least one antenna for transmitting and receiving an electromagnetic signal with at least several frequencies in the range of 5 Hz to 50 GHz, at least one sensor configured to measure a complex impedance by the at least one sensor influenced by the load constituted by the introduced container and its contents, representative of complex dielectric characteristics of the introduced container and its contents using said electromagnetic signal, and wherein said at least one of an audio and visual mechanism is also configured to provide information concerning the nature of the contents of said containers as a function of the complex measured impedance.

8. The device as claimed in claim 5, wherein said device further comprises at least one antenna for transmitting and receiving an electromagnetic signal with at least several frequencies in the range of 5 Hz to 50 GHz, at least one sensor configured to measure a complex impedance by the at least one sensor influenced by the load constituted by the introduced container and its contents, representative of complex dielectric characteristics of the introduced container and its contents using said electromagnetic signal, and wherein said at least one of an audio and visual mechanism is also configured to provide information concerning the nature of the contents of said containers as a function of the complex measured impedance.

* * * * *